United States Patent [19]
Nilsson

[11] Patent Number: 6,089,227
[45] Date of Patent: Jul. 18, 2000

[54] DEVICE FOR AN INHALER

[75] Inventor: Lars Gunnar Nilsson, Köping, Sweden

[73] Assignee: Microdrug AG, Hergiswil NW, Switzerland

[21] Appl. No.: 08/996,097

[22] Filed: Dec. 22, 1997

Related U.S. Application Data

[63] Continuation of application No. PCT/SE96/00807, Jun. 19, 1996.

[30] Foreign Application Priority Data

Jun. 21, 1995 [SE] Sweden .................................. 9502262

[51] Int. Cl.[7] .................................................. A61M 15/00
[52] U.S. Cl. ................................ 128/203.15; 128/203.12; 128/203.27; 239/102.2
[58] Field of Search ......................... 128/200.14, 203.12, 128/203.15, 202.25; 239/102.2

[56] References Cited

U.S. PATENT DOCUMENTS

| | | | |
|---|---|---|---|
| 4,788,016 | 11/1988 | Colclough et al. | 264/10 |
| 4,829,996 | 5/1989 | Noakes et al. | 128/200.14 |
| 5,033,463 | 7/1991 | Cocozza | 128/203.21 |
| 5,267,555 | 12/1993 | Pajalich | 128/200.14 |
| 5,497,764 | 3/1996 | Ritson et al. | 128/200.23 |
| 5,642,727 | 7/1997 | Datta et al. | 128/203.15 |
| 5,857,456 | 1/1999 | Sun et al. | 128/203.15 |
| 5,875,776 | 3/1999 | Vaghefi | 128/203.15 |
| 5,915,377 | 6/1999 | Coffee | 128/200.14 |

FOREIGN PATENT DOCUMENTS

| | | | |
|---|---|---|---|
| 9209322 | 6/1992 | WIPO . | |
| 9215353 | 9/1992 | WIPO . | |
| 94/14543 | 7/1994 | WIPO | 128/200.14 |
| 9419042 | 9/1994 | WIPO . | |

*Primary Examiner*—John G. Weiss
*Attorney, Agent, or Firm*—Young & Thompson

[57] ABSTRACT

An inhaler for electrical dosing of pure substances or preparates consisting of chemical and biological substances mainly used as drugs. The inhaler, which comprises a microprocessor thereby offers a flexible and measurable dose for the chemical and biological substances in the form of powders, or in the form of small drops or aerosols. The dosing is done electrically via first field generating member (23) whereby the substance is transmitted to a transmitting member which attracts the substance, from which the substance is then emitted by influence from another electrical field generated by a second field generating member (32), and the substance is finally mixed with air which is conventionally inhaled.

10 Claims, 3 Drawing Sheets

DEVICE FOR AN INHALER

This is a continuation of copending international application PCT/SE96/00807 filed Jun. 19, 1996, which designates the United States.

FIELD OF THE INVENTION

The present invention relates to a device for electrical dosing of pure substances, or preparations consisting of chemical and biological substances mainly used as drugs, whereby the substances to be dosed first of all are in the form of dry powders, but may also be in the form of small drops or aerosols.

BACKGROUND OF THE INVENTION

The dosing of drugs are carried out in a number of different ways in the medical service. In the medical service there are today for dry powders and aerosols a number of different inhalers in use, which all have as a common object to supply a substance to the lung through the patients own inspiration. The substances or mixtures of substances today used in the medical service are all developed to be supplied by means of a deep breath, which means high local velocities, which in turn means that a certain amount of the substance will stick to the airways and to the inhaler. The amount of substance in this way sticking also varies from individual to individual due to the individual way of breathing. This low efficiency and low dosing precision either means an increased risk for side effects if a too large dose is supplied, or risk for low effect if a too small dose is supplied. Thus, it is of the utmost importance that the dosing can be coordinated with the inspiration when using inhalers.

A method of improving the efficiency of an inhaler is disclosed in two patent documents, WO-9419042 and WO-9515353. The method means that the substance (powder or aerosol) is being electrically charged after the dosing and the distribution of the substance to the lung is in this way improved. The static electric charging of the substance is said to imply a more even distribution of the substance in the air stream at inspiration and therefore not sticking on to the inhaler or the airways to the same extent. The patent discloses a normal mechanical dosing. The inhalers of today, the usage of which increase strongly, accordingly do have a number of disadvantages which after all limit their efficiency and usage. The following list of items exemplifies some of these disadvantages:

A varying concentration of substance in the inhaled air.

A very large proportion of the substance sticks on to the inhaler and/or the airways.

Deviations in the inspiratory process can result in great deviations in the dose emitted to the lung.

Today, only a small number of substances can be used in inhalers according to prior art.

The amount of substance emitted to the lung can vary from patient to patient and between different dosing occasions.

Inhalers according to prior art are generally not meant for repeated reuse.

DESCRIPTION OF THE INVENTION

The present invention relates to a device for electrical dosing of pure substances or preparations consisting of chemical and biological substances, which substances are mainly used as medicaments. The substances to be dosed are mainly in the form of dry powder, but may also be in the form of droplets or aerosols.

In particular, the present invention is meant to be applied at the construction of a new continuous inhaler, which thereby gives a number of advantages in comparison to inhalers according to prior art which are found on the market today.

The invention according to the independent claim 1 relates to a device in a continuous inhaler with a capacity of dosing a great number of different substances. With continuous inhaler is meant an equipment allowing a substance to be supplied continuously or by a repeated number of small doses with such a frequency that the result from the inhaler can be characterized as continuous. Dosing is connected to the air flow and the concentration and amount is controlled during the inspiratory process. This means a more even supply of substance and thereby a possibility to increase the amount of substance to the lung compared to the inhalers existing today.

The inhaler thus created is suitably equipped so as to be programmable to be directly flexible to the special preconditions of every patient with respect to inspiratory characteristics, need of substance, number of doses and dosing intervals. The new inhaler is first of all meant to be portable, but may also be stationary.

The dependent claims 2 to 13 relate to different embodiments of the present invention.

DESCRIPTION OF THE DRAWINGS

The invention will be described in terms of a preferred and illuminating embodiment taking reference to the appended drawings where like reference symbols denote like or corresponding element, where.

AN ILLUSTRATIVE EMBODIMENT

1. Technical description

The substances which are to be dosed are mainly in the form of dry powder, but may also be in form of small drops and aerosols. Henceforth, in connection with the description of an illustrative embodiment powder will be used as a common name for all types of substances or preparations of substances which are to be dosed.

Figure 1:
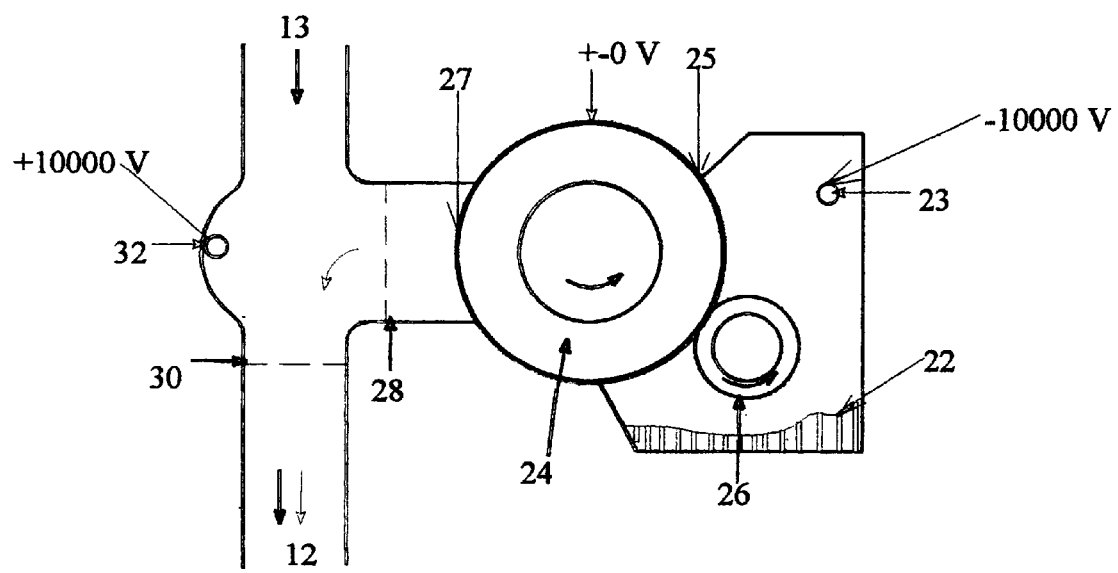
FIG. 1 shows an outline sketch of the function of an inhaler in accordance with the present invention.

In FIG. 1 an outline sketch illustrating the invention in a simple way is shown. To the right in the sketch is provided a space 22 for storing the powder. In the same space an electric field is generated by means of an electrode device 23, which is given a suitable electric potential. The object of the electric field is the static charging of the powder particles. Said particles are then attracted to and sticking on to a rotating dosing drum 24 having the electric potential of approximately +/−0 V. During the rotation superfluous powder is removed by means of a smoothing device 25. When the drum has completed half a revolution the powder will be exposed to a second electric field generated by a second electrode device 32 with a suitable opposite potential, whereby the powder is loosened and moved away from the drum 27 to an air stream 13, which is obtained from an inspiration, and is then mixed with said air stream and further transported out through the inhaler nozzle 12. On its way the powder passes an electronic grid 28 for the regulation of the dosing and a deionizing zone 30. The correct dose in form of a homogenous air/powder mixture then passes out through the mouth piece or nozzle 12.

Figure 2:
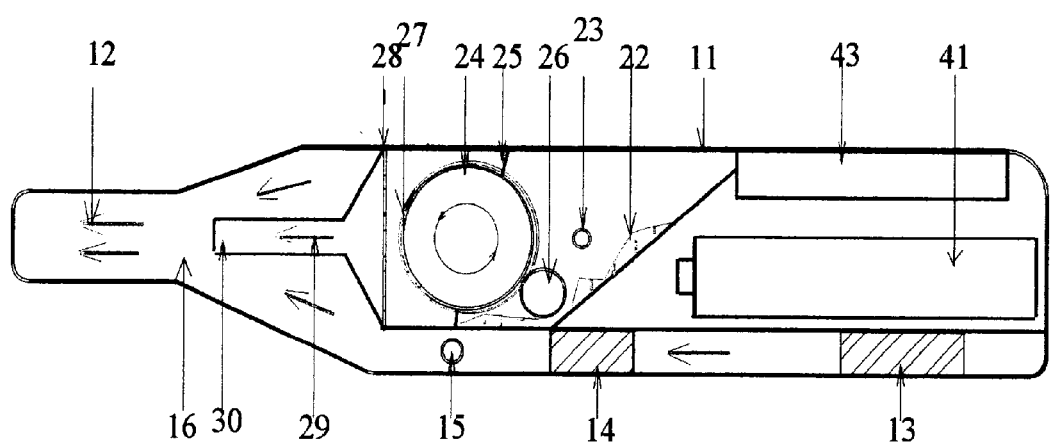
FIG. 2 shows a side view of an illuminating embodiment of the inhaler constructed in accordance with FIG. 1.
Figure 3:
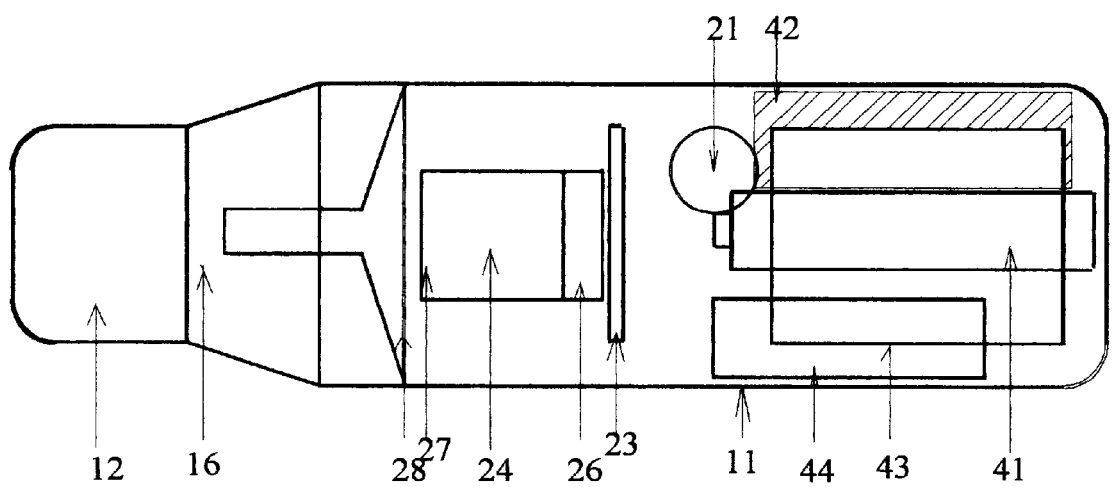
FIG. 3 shows the inhaler according to FIG. 2 in a view from above.

In FIGS. 2 and 3 an illustrative embodiment of an inhaler in accordance with the present invention is shown. The inhaler has a cover 11, which is completely closed in order to prevent dust and moisture from penetrating. When choosing the material for the manufacturing of the cover 11 and other mechanical parts the electric properties of the material is suitably devoted special attention in order to prevent the accumulation of powder in the wrong places. Also the cover 11 is preferably constructed with such a design that the least possible amount of powder can stick. The size of the inhaler is thus adapted that it can be carried in for example the pocket of a jacket. Inspiration is done through a nozzle 12 in the front portion of the inhaler and the air is at inspiration sucked in through a filter 13 on the underside of the inhaler. During the passage through the inhaler another filtration 14 and the measurement of the air velocity 15 takes place before the air is mixed with powder in the diffusor 16 in front of the nozzle 12.

The powder, which is stored in a cartridge, which may also contain a drying agent to ensure a correct level of humidity, is supplied to the inhaler through an opening 21 (see FIG. 3) on top of the inhaler. The opening is hermetically shut after the charging. The powder cartridge is preferably designed such that it automatically opens at the loading so that the powder is discharged in the storing space 22 of the inhaler and that also the closing takes place in the same operation. The amount of powder is adapted to the needs of the patient and can normally cover for example a complete period of treatment. In the storing space 22 of the powder there is an electrode 23, which when the inhaler is to be used is charged to a suitable voltage and then generates a field which in turn charges the powder particles to a suitable electrostatic potential. In the same space, further, a rotating dosing drum 24 with a different potential is provided, to which the powder particles will be attracted and stick. In order to obtain a smooth layer of powder on the cylinder a smoothing device 25 is provided. For cleaning the drum before the surface is coated with powder, a cleaning device 26, e.g., in the form of a rotating brush, is provided. When the dosing drum 24 rotates and the smoothed powder comes over to the other side 27 of the drum the powder will be influenced by a second electric field of an opposite potential, which thereby loosens the powder and transports it in the direction away from the drum. On the way to the nozzle 12 the powder passes through an electric grid 28 which regulates the amount of powder emitted from the dosing drum 27 and subsequently through a pipe containing a powder accelerator 29 and possibly a deionizing zone 30. After this the powder mixes with the inhaled air in a diffusor 16.

All the regulation, monitoring and memory functions are handled by a microprocessor 42 which is connected to a function indicator 43. Prior to the usage of the inhaler in order to provide correct dosing as well as providing correct control of the different functions of the inhaler the microprocessor is programmed through an external connection in accordance with prior art, so that an optimum result is to be achieved.

To supply the inhaler with power a rechargeable battery 41 is provided, which by means of an external switch on the cover of the inhaler can be switched on and off. For the driving of the mechanical equipment a motor 44 is supplied, which is coupled, among other things, to the driving means of the dosing drum in a way which is known in the art.

2. A mode of operation.

The function of the inhaler is based on dosing by means of the electric charging of a powder in a way which is described in the literature concerning modern printers and copy machines. The principle is illustrated in FIG. 1 and can briefly be described in the following way.

The powder 22 is statically charged by means in an electric field which is generated by an electrode device 23 with a suitable voltage. The powder will then be attracted to a device, in this case a rotating dosing drum 24, which has a potential of approximately +/−0 V. The drum 24 will in this way continuously be coated with a thin layer of powder. On the opposite side 27 of the drum a suitable amount of powder is loosened by means of an electrode device 32 with an suitable opposite potential. The in this way dosed amount of powder is then drawn away and mixed by means of the air stream resulting from the inspiration, and continues through the inhaler and down into the patients lung system. The amount of powder emitted from the dosing position is regulated in many ways, for example by means of an electronic grid 28. If necessary, deionizing 30 takes place before the air/powder mixture leaves the inhaler 12. The loosening of a powder can be accomplished either intermittently in small doses which through the volume coming out from the inhaler will be understood as continuous, or through a truly continuous process where the dose is continuously emitted.

The demands on the electric properties of the powder are specific in the same way as when powder is dosed in a printer. To obtain the correct electric properties it is sometimes necessary to make some sort of preparation of the powder prior to usage. This preparation could for example be a micronisation of the powder to the correct size, preparations together with carriers having the right electric properties and or a surface treatment of the powder. An adaptation to the properties of the powder can also be done through choosing a suitable method for the electrostatic charging of the powder. Examples of different types of charging procedures are coronacharging, tribocharging and inductive charging. The charging procedure is connected to the microprocessor of the inhaler which is thereby programmed in a way known in the art in order to achieve an optimum result.

The amount of powder emitted is through the microprocessor connected to the air velocity through the inhaler in order to provide an as even as possible dose throughout the dosing process. This is advantageous since it means less powder deposits in the mouth and in other parts of the airways resulting from this procedure. The amount of air is measured by means of an airflow gauge 15 and the amount of powder is measured and dosed electrically by means of the electronic grid 28. The micro processor 42 stores and processes the results from the measurements throughout the dosing process in order to secure a correct emitted dose from the inhaler. By means of a function indicator 43 the inhaler warns if the inhalation should be incorrect, and for example too low a dose has been emitted. If a correct dose is emitted the inhaler gives a clearance and verifies and stores the emitted total dose.

After being emitted from the dosing equipment, depending on its properties, the powder may need some after-treatment as for example deionization 30, but also deagglomeration, separation of carriers and so forth, which is then carried out in the dose treatment member 29 of the inhaler, located in the flow direction subsequent to the dose emittance means. The dose treatment member is suitably equipped in accordance with the demands set by each powder.

Subsequent to being after-treated in the dose treatment member 29, 30 the powder is emitted through the nozzle 12 of the inhaler into the mouth of the patient for further transportation down into the lung. The nozzle 12 is designed so as to give the least possible substance deposit on teeth and in the oral cavity as well as achieving the least possible difference in air velocity between the inhaler and the oral cavity in order to minimize the ejector effect and thereby minimizing the risk for the substance being "shot" at the mucous membrane in the oral cavity. The nozzle 12 can be designed in alternatives ways to suit other types of administration of powder. In order to avoid the patient and the inhaler having different electric potentials at the inhalation, the nozzle of the inhaler is provided with an electrically conductive portion which is in contact with the patients mouth at the inhalation. In the case of different potentials the risk of powder deposits in the oral cavity or the upper airways increases.

Thus, the purpose of the inhaler according to the present invention is that no extra heavy breath shall be needed when inhaling but only, basically, a continuously normally calm but suitably deep breath. Inhalation of the at the time preferred total dose can, if necessary, thereby also take place by means of a number of subsequent breaths whereby the inhaler in accordance with the invention automatically regulates the dispensing of a correct amount of powder.

When the switch of the inhaler is put in the "on" position it automatically enters the stand-by position. The inhaler is then put to the mouth and when the inspiration starts the air flow sensor gives a signal to the micro processor, which immediately starts the dosing of the powder. Then, the micro processor controls the dosing process throughout the inspiration and makes sure that the correct dose has been emitted. When the patient has switched off the inhaler after usage, it is shut by for example placing a tight hood over the air intake as well as over the nozzle, thereby protecting the container of the substance, as well as all other moist sensitive details, from from moisture. The inhaler can therefore be brought in for example the pocket of a jacket or in a purse. The inhaler, which must always be personal, can thereby give the physician a possibility of following up the usage of the inhaler and the doses taken by the patient.

The micro processor is preferably programmed by means of one or more sample inspirations done by the patient, the characteristics of which is registered by and stored in the micro processor. This programming means that the dosing can be completely adapted to the inspiratory characteristics of every patient.

The regeneration of the inhaler with new powder is achieved by the insertion of a new powder cartridge in the inhaler and the resetting of the micro processor 42 of the inhaler. The battery 41 of the inhaler is in the preferred embodiment in itself an exchangeable but also rechargeable battery, which at suitable occasions is connected for recharging by means of a standard recharging device well known in the art and commercially accessible to the public.

What is claimed is:

1. A device for an inhaler, comprising a power source for the creation of suitable electric potentials for the administration of substances, wherein dosing is achieved by an electrostatic charging of the substance via a first field generating member (23), the substance being transmitted to a transmission member, which attracts said substance, from which transmission member the substance is emitted by the influence of an additional electric field generated by a second field generating member (32), the transmission member comprising a dosing drum (24), which during rotation by a built-in motor (26) will emit the substance by the influence from the additional electric field generated by the second field generating member (32).

2. The device according to claim 1, wherein the substance is emitted from a dosing drum (24) in the device by a combination of the additional electric field and an air stream resulting from inspiration.

3. The device according to claim 1, wherein the inhaler is additionally inspiration controlled, whereby no substance is emitted from the dosing drum (24) until an air stream has been detected by means of an air flow gauge (15).

4. The device according to claim 1, wherein the inhaler is furthermore provided with an accelerator member (29), a deionizing member (30) and a diffusor member (16), which are included in a nozzle member.

5. The device according to claim 1, wherein the inhaler is provided with a micro processor (42) which can be programmed for the control of dosing, flows, time, number of doses, limits, and security codes, which furthermore enables an advanced follow up of the patient usage of the substance or substances during a period of time signaling overdosing, faulty usage or trends.

6. The device according to claim 1, wherein the inhaler is provided with a function indicator (43) which warns in the case of risk for overdosing or faulty usage and also gives clearance in case of a dose correctly emitted and received by the patient.

7. The device according to claim 1, wherein the substance is electrostatically charged by tribocharging or inductive charging to a potential.

8. The device according to claim 1, wherein the inhaler is coupled with the person performing the inspiration thereby decreasing the risk of substance depositing in the mouth and in the upper airways.

9. The device according to claim 1, wherein the substances which are dosed are thus prepared that their electrical characteristics are suited for the electric dosing.

10. The device according to claim 1, wherein the substance is a powder and the electrical characteristics of the powder are optimized by the addition of carriers, or by surface treatment of the powder, and wherein a correct particle size and particle structure is used.

* * * * *